US006335470B1

(12) United States Patent
Darsow et al.

(10) Patent No.: US 6,335,470 B1
(45) Date of Patent: Jan. 1, 2002

(54) METHOD FOR PRODUCING VARIABLE MIXTURES OF CYCLOHEXYLAMINE AND DICYCLOHEXYLAMINE

(76) Inventors: Gerhard Darsow, Zu den Tannen 39, D 47804 Krefeld (DE); Reinhard Langer, c/o Bayer Aktiengesellschaft, D 51368 Leverkusen (DE)

(*) Notice: Subject to any disclaimer, the term of this patent is extended or adjusted under 35 U.S.C. 154(b) by 0 days.

(21) Appl. No.: 09/555,755

(22) PCT Filed: Nov. 26, 1998

(86) PCT No.: PCT/EP98/07629

§ 371 Date: Jun. 2, 2000

§ 102(e) Date: Jun. 2, 2000

(87) PCT Pub. No.: WO99/29654

PCT Pub. Date: Jun. 17, 1999

(30) Foreign Application Priority Data

Dec. 9, 1997 (DE) .................................... 197 54 571

(51) Int. Cl.[7] ............................................ C07C 209/72
(52) U.S. Cl. ...................................................... 564/450
(58) Field of Search ......................................... 564/450

(56) References Cited

U.S. PATENT DOCUMENTS 3,636,108 A    1/1972   Brake ................... 260/563 D
4,952,549 A *  8/1990   Immel et al. ............ 502/330
5,023,226 A    6/1991   Immel et al. ............ 502/313
6,043,395 A *  3/2000   Langer et al. ........... 564/450

FOREIGN PATENT DOCUMENTS

| DE | 805 518    | 5/1951 |
| DE | 1 106 319  | 5/1961 |
| EP | 053 818    | 6/1982 |
| EP | 501 265    | 9/1992 |
| EP | 503 347    | 9/1992 |
| EP | 560 127    | 9/1993 |
| FR | 1530477    | 6/1968 |
| GB | 969542     | 9/1964 |
| WO | 98/15351   | 4/1998 |

OTHER PUBLICATIONS

Derwent Japanese Jan. 2, 1968, vol. 7, No. 5, Japanese Patent 68–3180–Cyclohexylamine prepn.

* cited by examiner

*Primary Examiner*—Sreeni Padmanabhan
*Assistant Examiner*—Brian J. Davis
(74) *Attorney, Agent, or Firm*—Joseph C. Gil; Richard E. L. Henderson

(57) ABSTRACT

Ru/Pd catalysts on supports are used for the preparation of mixtures of substituted or unsubstituted cyclohexylamine and substituted or unsubstituted dicyclohexylamine in variable amounts by catalytic hydrogenation of substituted or unsubstituted aniline at elevated temperature and elevated $H_2$ pressure. These catalysts are characterized in that they contain no halogen or sulphur compounds.

8 Claims, No Drawings

METHOD FOR PRODUCING VARIABLE MIXTURES OF CYCLOHEXYLAMINE AND DICYCLOHEXYLAMINE

This application is a 371 of PCT/EP98/07629 filed Nov. 26, 1998.

The invention relates to a process for preparing mixtures of substituted or unsubstituted cyclohexylamine and substituted or unsubstituted dicyclohexylamine in variable ratios by catalytic hydrogenation of substituted or unsubstituted aniline by means of hydrogen at elevated temperature and elevated pressure using catalysts comprising a support which may be doped with oxides, hydroxides and hydrated oxides of the rare earths (REs) and of manganese and to which Ru and Pd have been applied, the catalysts being characterized in that they contain no halogen or sulphur compounds. Substituted or unsubstituted cyclohexylamines and dicyclohexylamines are used for producing ageing inhibitors for rubbers and plastics, as corrosion inhibitors in aqueous solution and as intermediates for textile assistants and crop protection agents.

It is known that cyclohexylamine can be prepared by pressure hydrogenation of aniline. This hydrogenation is carried out using mainly noble metal catalysts, for example an Ru catalyst moderated with alkali metal as described in U.S. Pat. No. 3,636,108, where $NH_3$ and preferably a solvent are additionally used. A further process for the pressure hydrogenation of aniline to give cyclohexylamine is described in DE-B 1 106 319, in which an Ru catalyst is likewise used. In this process, dicyclo-hexylamine formed as coproduct is added to the starting, material again. However, owing to the simultaneous formation of cyclohexane, the process achieves only a moderate yield. According, to EP-A 53 818, supported Pd catalysts are better than Ru catalysts; the catalysts described there contain additives which either come from a group of basic compounds of the alkali metals, alkaline earth metals and rare earth metals or a group consisting of the metals Fe, Ni, Co, Mn, Zn, Cd and Ag. These catalysts allow the reduction of substituted anilines to give the corresponding cyclohexylamines; however, the corresponding dicyclohexylamines are completely absent. This applies similarly to Co catalysts containing a basic additive (GB 969 542) and to Raney Co (JP 68/03 180).

In the processes for the pressure hydrogenation of aniline which have been described, the dicyclohexylamine is formed only as by-product in addition to cyclohexylamine or not at all. In order to obtain dicyclohexylamine in larger amounts, it is prepared by separate processes. Thus, for example, it can be obtained by pressure hydrogenation of diphenylamine using an $Ru/Al_2O_3$ catalyst (DE-B 1 106 319 above). Dicyclo-hexylamine is also formed in the reaction of cyclohexanone with cyclohexylamine in the presence of Pd on carbon under a hydrogen pressure of 4 bar (ER 1 530 477). In a cumbersome process, dicyclohexylamine can be isolated from the hydrogenation product of aniline over an Ni catalyst by fractional condensation. From the residual mixture, part of the ammonia also formed is removed and the remainder is returned to the reaction (DE-C 805 518).

EP-A 501 265 discloses a process for preparing substituted or unsubstituted cyclo-hexylamine and substituted or unsubstituted dicyclohexylamine by catalytic hydrogenation of substituted or unsubstituted aniline using a catalyst containing Ru, Pd or a mixture of both metals which have been applied to a support comprising niobic acid or tantalic acid or to a mixture of both. EP-A 503 347 discloses a further process for preparing substituted or unsubstituted cyclohexylamine and substituted or unsubstituted dicyclohexylamine by hydrogenation of an appropriately substituted aniline using a catalyst formed by first treating an α- or γ-$Al_2O_3$ as support with at least one compound of rare earth metals and with at least one compound of manganese and then treating this with at least one Pd compound.

However, all catalysts and processes mentioned still have disadvantages in respect of conversion, selectivity, catalyst life, necessity of using $NH_3$, etc.

The problems which still occur today despite the progress which has occurred are demonstrated by EP 560 127 filed in 1992: the Ru—Pd catalysts on alkaline supports used here can hydrogenate aromatic amines at low pressure, but only a small throughput of from 0.03 to 0.05 g/ml of catalyst and hour is possible, which requires large amounts of catalyst and large reactors; $NH_3$ has to be added in large amounts and the temperatures are held in the vicinity of 160° C. Nevertheless, hydrogenolysis still occurs at continuing incomplete conversion, recognizable by the formation of benzene and cyclohexane; the selectivity leaves something to be desired and the operating life of the catalysts is significantly less than, for example, that in EP 324 983. The commencement of deactivation of the catalyst is indicated by the slowly falling conversion.

It was therefore an object of the invention to provide catalysts for the industrial hydrogenation of aromatic amines to give cycloaliphatic amines, which catalysts, at a high space velocity over the catalyst, give complete conversion, have high selectivity in respect of the formation of primary and secondary cycloaliphatic amines, have a long life and, in particular, no longer trigger hydrogenolysis and methanization of the substrates.

It has been found that these requirements can be met when use is made of catalysts which contain Ru and Pd and are preferably applied to supports or to RE-Mn-doped supports and are strictly halogen-free and sulphur-free. The invention is surprising in that the influence of halogen and sulphur compounds on the catalytically active Ru in the abovementioned sense of undesired over-activation which causes hydrogenolysis and methanization was not known. The invention is also surprising since, obviously, even small residual amounts of halogen and sulphur compounds which remain in the catalyst after the preparation of such catalysts from starting materials containing halogen and sulphur compounds cause this undesirable property.

The invention provides a process for preparing mixtures of cyclohexylamines (II) and dicyclohexylamines (III) of the formulae:

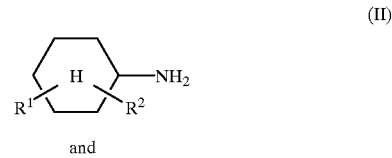

and

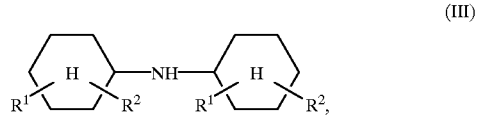

in variable ratios by catalytic hydrogenation of aromatic amines of the formula (I):

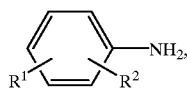
(I)

where, in the formulae, $R^1$ and $R^2$ are independently hydrogen, $C_1$–$C_4$-alkyl or $C_1$–$C_4$-alkoxy, at a reaction temperature of from 100 to 350° C. and a pressure of from 10 to 400 bar, which is characterized in that the catalysts used are fixed-bed catalysts which contain, as active constituents, a total of from 0.05 to 10% by weight of Ru and Pd in a ratio Ru:Pd= 1:30–30:1 on supports and are free of halogen and sulphur compounds.

For the purposes of the invention, halogen-free means that the catalysts contain no halogen, i.e. no F, I, Br and particularly no Cl, and are therefore advantageously prepared from starting materials which do not contain halogen. For the purposes of the invention, free of sulphur compounds means that the catalysts contain no S and are therefore advantageously prepared from starting materials which are free of sulphur compounds. The sum of the halogen and sulphur contents of all starting materials for preparing the catalyst is therefore <0.8% by weight, preferably <0.3% by weight, particularly preferably <0.1% by weight, with inclusion of the complete absence of halogen and sulphur, based on their total amount. This means that the catalytically active positions, in particular the RE—Mn coating and the noble metals, are halide-free and free of sulphur compounds.

Starting compounds for preparing the catalysts used according to the invention are therefore halogen-free and sulphur-free compounds of Ru and Pd and, if they are present, of REs and Mn or low-halogen/low-sulphur compounds within the above-mentioned specification. Examples which may be mentioned are the nitrates, acetates, organic complexes with acetylacetone or amino acids.

Supports for the catalysts used according to the invention are aluminas, $Al_2O_3$ in its various modifications ($\alpha$, $\zeta$, $\eta$, $\gamma$), preferably the $\gamma$ modification, also supports otherwise customary for noble metals, e.g. $TiO_2$, kieselguhr, silica gel, $BaCO_3$, $CaCO_3$, ZnO, MgO, pumice, $ZrO_2$ and naturally also the oxides or hydrated oxides of Mn and REs, preferably $TiO_2$, $BaCO_3$, MgO and $Al_2O_3$, particularly preferably $Al_2O_3$ in the $\gamma$ modification, and also oxides or hydrated oxides of Mn and REs. However, in the abovementioned manner, Mn and REs are predominantly used for doping other supports.

For the purposes of the present invention, REs are the elements of transition group III of the Periodic Table (Mendeleev), for example scandium, yttrium, lanthanum and the lanthanides. As RE, it is possible to use either one of the elements mentioned or a mixture of a plurality of them. This is particularly important because it is also possible to use crude mixtures of REs as are industrially available and are initially enriched in only one or two of the REs. Preference is given to using one or more of the elements selected from the group consisting of yttrium, lanthanum, cerium, praseodymium, neodymium and dysprosium. Particular preference is given to using cerium and/or lanthanum. Very particular preference is given to using cerium, possibly in a mixture enriched in cerium. For application to the support, the REs and manganese are in the form of their compounds, preferably in oxide form.

To prepare the catalysts, the procedure can be to apply the noble metals in the form of suitable salts, either together or in separate steps, to one of the abovementioned supports in the form of extrudates, pellets, spheres or granules having a diameter of from 1 to 10 mm and to carry out a drying step after each application.

Drying is carried out in a known manner, e.g. at from 30 to 200° C. under reduced or atmospheric pressure (from 1 to 1000 mbar), for instance in a water pump vacuum.

In the preparation, preference is given to using aqueous solutions. However, it is also possible to use, or make concomitant use of, organic solvents such as lower alcohols, lower carboxylic acids, lower nitriles, amides and lactones having 1–6 carbon atoms, as long as the starting materials are soluble therein. The noble metals are applied in amounts of from 0.05 to 10% by weight, preferably from 0.1 to 5% by weight, with these contents being based on the total weight of the catalyst.

Ru and Pd are present in a weight ratio of from 1:30 to 30:1, preferably from 1:10 to 10:1, particularly preferably from 2:8 to 8:2. Up to 20% by weight of the amount of Ru and Pd can be replaced by other noble metals such as Pt, Ir, Rh, Ag and Au.

If a support is first doped with REs and Mn, this can be achieved, for example, by impregnating or spraying the support with solutions of suitable salts of these elements. On heating at temperatures from about 200 to 450° C., the salts of RE and Mn are converted into oxidic compounds adhering to the support. However, the application of the compounds of REs and Mn can also be carried out by co-precipitation of RE and Mn hydroxide mixtures on the impregnated support by means of alkalis, alkaline earths or $NH_3$ and subsequent washing out of soluble components by means of water. The support which has been pretreated in this way is dried and then preferably heated for from 1 to 120 hours at from 200 to 450° C., preferably from 250 to 430° C., with the temperature also being able to be gradually increased within the range indicated. Use is made, for example, of the acetates or nitrates of REs and Mn.

The support which has been prepared in this way is subsequently impregnated or sprayed with solutions of the noble metals Ru and Pd. For this purpose, for example, the acetates and nitrates are used. This application of the noble metals can be carried out in one step using dissolved mixtures of the salts or successively using solutions of the individual compounds. After each application, the catalyst should be dried. Before use, the catalysts are advantageously activated by means of hydrogen in the reactor at from 80 to 350° C.

The process of the invention is carried out at pressures of from 10 to 400 bar and temperatures of from 100 to 350° C. It can be carried out batchwise in an autoclave, but preferably continuously in the gas phase or trickle phase. The space velocity over the catalyst is advantageously from 0.1 to 3 g/ml·h, preferably from 0.2 to 2.5 g/ml·h, particularly preferably from 0.3 to 2.0 g/ml·h. The hydrogen present can represent the total pressure of 10–400 bar, but it is also possible to employ a mixture of $H_2$/inert gas ($N_2$, $CH_4$, Ne, Ar or a plurality of these). In all cases, $H_2$ is present in an amount which is from 2 times to 100 times, preferably from 10 times to 40 times, the amount necessary for the hydrogenation.

Should, for particular reasons, a proportion of $NH_3$ in the reaction mixture be advantageous, it can be introduced without difficulties.

Suitable starting materials are unsubstituted aniline or substituted anilines of the formula (I),

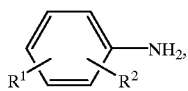

(I)

reaction products are cyclohexylamines (II) or dicyclohexylamines (III) of the formula:

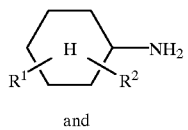

(II)

and

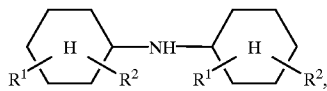

(III)

where, in the formulae, $R^1$ and $R^2$ are independently hydrogen, $C_1$–$C_4$-alkyl or $C_1$–$C_4$-alkoxy.

The ratio of the two amines can be changed as a function of the hydrogenation temperature, so that more substituted or unsubstituted cyclohexylamine is formed with increasing temperature and the opposite effect is achieved with decreasing temperature.

The process of the invention can be carried out continuously in the gas phase or the trickle phase using fixed-bed catalysts, with at least 2 times the molar amount of hydrogen per mol of starting material passing through the reactor during the course of the process. Preference is given to working in the trickle phase. The hydrogenation reactors can be single high-pressure tubes of steel or a steel alloy which are completely or partly filled with shaped catalyst bodies; in the case of relatively large tube cross sections, the use of the shaped bodies on trays such as wire baskets or similar internal fittings may be useful. Furthermore, it is also possible to employ a high-pressure tube bundle within an overall casing; again, the individual tubes are completely or partly filled with the shaped catalyst bodies.

The catalysts are reduced by means of hydrogen and thus activated. This can in principle be done simultaneously with the hydrogenation of the starting material used, but in this case a longer running-in phase is necessary before the catalysts reach their full activity and the highest possible space-time yield is therefore achieved. This activating reduction with hydrogen is carried out in the temperature range of 100–350° C. and in the pressure range of 10–400 bar. In this procedure, the atmospheric oxygen which is initially present is first removed completely by means of an inert gas such as nitrogen, argon, methane or ethane before a proportion of 10–15% by volume of hydrogen is added to the inert gas. For reasons of its ready availability, the inert gas is preferably nitrogen. Within a fixed period of time, for example 24 hours, the proportion of inert gas is then steadily reduced and finally the inert gas is removed completely so that the activation and reduction is carried out using pure hydrogen. The reduction is complete when the catalyst no longer consumes any hydrogen and consequently no more water of reaction is formed.

The substituted or unsubstituted aniline used can be diluted with a suitable reaction-inert solvent, for example with cyclohexane or cyclohexanol, in an amount of 10–100% by weight, preferably 10–40% by weight, based on the weight of the substituted or unsubstituted aniline. The addition of cyclohexanol in the indicated amount, which can also be replaced completely or partially by cyclohexanone or phenol, also makes it possible to trap the ammonia liberated in the process by amination and to form further substituted or unsubstituted cyclohexylamine/dicyclohexylamine. In the continuous procedure in the trickle phase it can be useful not to hydrogenate the substituted or unsubstituted aniline used to completion, but to aim for a degree of conversion of 80–97%.

The catalysts used according to the invention display long operating lives: up to now >6000 hours have been observed in experiments which were stopped without a noticeable decrease in the activity. These operating lives are several times as high as those described in the abovementioned EP-A 501 265 and EP-A 503 347.

The reaction mixtures obtained after the hydrogenation do not contain any cyclohexane, unless this has been added as solvent, so that particularly high yields of substituted or unsubstituted cyclohexylamine and substituted or unsubstituted dicyclohexylamine can be achieved. The hydrogenation mixtures can be worked up by simple distillation. For such a work-up, it can be advantageous not to react the substituted or unsubstituted aniline to completion. The incompletely reacted aniline can be returned to the reaction. The unconsumed proportion of the hydrogen added in a from 2-fold to 100-fold molar excess can also be returned to the reaction, in which case the major part of the unreacted hydrogen is advantageously recovered in a high-pressure separator, so that the work of compression for the hydrogen does not have to be performed once again.

The substituted or unsubstituted cyclohexylamine and substituted or unsubstituted dicyclohexylarnine prepared according to the invention are obtained in a purity of at least 99.9% by weight after separation by distillation. In this purity, the said compounds are generally usable for all manner of farther processing.

The variability of the process of the invention is shown by a strong increase in the proportion of substituted or unsubstituted dicyclohexylamine compared to the substituted or unsubstituted cyclohexylamine with increasing temperature under otherwise identical conditions. Thus, for example, the proportion of substituted or unsubstituted dicyclohexylamine obtained in the temperature range from about 240 to 260° C. is more than 4 times that obtained at a temperature of 190° C.

EXAMPLES

Example 1

(Preparation of a catalyst support)

5.0 1 (4.01 kg) of a commercial γ-$Al_2O_3$ having a BET surface area of 310 $m^2$/g as spheres having a diameter of from 2 to 5 mm (SPH 501 from Rhone-Poulenc) were stirred with 1.89 1 of an aqueous solution of 248 g of Ce($NO_3$)$_3$·6 $H_2O$ and 365.5 g of Mn ($NO_3$)$_2$·4 $H_2O$ until the solution had been completely absorbed, and were then dried at 100° C. under reduced pressure. At the end of the preparation, the catalyst support was calcined first for 3 hours at 300° C. and subsequently for 4 hours at 400° C.

Example 2

4000 g of a catalyst support prepared as described in Example 1 were impregnated with 133.3 g of Pd ($CH_3CO_2$)$_2$ (48% by weight Pd) in 1 383 g of acetonitrile, dried (3 h, 40°

C., N₂) and reduced with hydrogen at 100° C. for 3 hours under a pressure of 300 bar. Subsequently, a solution of 49 g of Ru(NO₃)₃ (32.6% by weight Ru) in 1 383 g of H₂O was applied in the same way, and the impregnated support was dried and reduced with hydrogen for 3 hours at 100° C. under a pressure of 300 bar.

Example 3

(Comparative Example)

100 g of the Ce—Mn-doped support from Example 1 were impregnated with 10.67 g of Na₂PdCl₄ (15% by weight Pd) in 27 g of water, dried and reduced with hydrogen for 3 hours at 100° C. under a pressure of 300 bar. In the same way, the support was subsequently impregnated with 2.00 g of RuCl₃ (20% Ru) in 34 g of water, then dried and reduced as above.

Example 4

(Comparative Example)

180 g of a catalyst support prepared as described in Example 1 were impregnated with 11.04 g of Ru (NO₃)₃ (32.62% by weight Ru) in 11.7 g of water, dried and reduced with hydrogen as above for 3 hours at 100° C. under a pressure of 300 bar.

Example 5

An upright, thermally insulated high-pressure tube of stainless acid-resistant steel which had an internal diameter of 45 mm and a length of 1 m and had previously been flushed free of oxygen by means of nitrogen was charged with 1.4 of catalyst which had been prepared as described in Example 2. The tube was subsequently flushed with hydrogen until the nitrogen had been removed. The hydrogen pressure was then increased to 300 bar, the reaction temperature was set to the desired value and the injection of aniline which had been heated to a temperature of 160° C. in an upstream, electrically heated heat exchanger before entry into the reaction tube was commenced. 700 g/h of aniline together with 10 standard m³/h of hydrogen were pumped through the reaction tube in a descending manner from the top to the bottom. The reaction product leaving the reaction tube was cooled to a temperature of <60° C. in a second heat exchanger (water cooler) under a hydrogen pressure of 300 bar and was separated from excess hydrogen in a gas separator. After further cooling to a temperature of <30° C. and depressurization to atmospheric pressure, the reaction product was analysed by gas chromatography. Under steady-state reaction conditions, the following product composition was obtained as a function of the reaction temperature (figures in % by area, ANI=aniline, BEN=benzene, CYH=cyclohexane, CHA=cyclohexylamine, DCHA=dicyclohexylamine, R=remainder):

| Temperature ° C. | ANI % by area | BEN % by area | CYH % by area | CHA % by area | DCHA % by area | R % by area | Loss BEN/CYH/R % |
|---|---|---|---|---|---|---|---|
| 190 | 2.71 | — | 0.10 | 80.79 | 15.17 | 1.23 | 1.39 |
| 200 | 0.01 | — | 0.11 | 60.02 | 39.11 | 0.75 | 0.86 |
| 210 | — | — | 0.14 | 54.16 | 44.87 | 0.83 | 0.97 |
| 220 | — | — | 0.26 | 46.70 | 52.36 | 0.68 | 0.94 |
| 230 | — | — | 0.28 | 35.51 | 63.62 | 0.59 | 0.87 |
| 240 | — | — | 0.38 | 29.62 | 69.25 | 0.75 | 1.13 |
| 260 | — | — | 1.31 | 29.14 | 68.76 | 0.79 | 2.10 |
| 280 | — | 0.05 | 4.92 | 36.76 | 56.67 | 1.60 | 4.97 |
| 300 | — | 0.20 | 8.15 | 41.31 | 47.99 | 2.35 | 10.70 |

The variable ratios of CHA and DCHA achieved in the above table are based on the use of fresh hydrogen. If the hydrogen excess and with it also the main part of the NH₃ formed are returned to the hydrogenation system, the following temperature-composition is obtained:

| Temperature ° C. | ANI % by area | BEN % by area | CYH % by area | CHA % by area | DCHA % by area | R % by area | Loss BEN/CYH/R % |
|---|---|---|---|---|---|---|---|
| 190 | 9.72 | — | 0.19 | 63.13 | 26.19 | 0.77 | 0.96 |
| 200 | 4.83 | — | 0.15 | 59.25 | 34.87 | 0.90 | 1.05 |
| 210 | — | — | 0.20 | 53.87 | 45.22 | 0.71 | 0.91 |
| 220 | — | — | 0.19 | 47.49 | 51.96 | 0.36 | 0.45 |
| 230 | — | — | 0.37 | 45.01 | 54.29 | 0.33 | 0.70 |
| 240 | — | — | 0.57 | 42.97 | 55.95 | 0.51 | 1.08 |

In both tables, the proportions of benzene and cyclohexane and also of remaining organic compounds are low, as is desired. The sum of products which cannot be reused (loss) is correspondingly low. Analyses of the H₂- and NH₃-containing waste gas have shown that no hydrogenolysis to pentane, butane, propane, ethane and methane occurs in the temperature range up to 240° C. None of these substances could be found in the waste gas. At higher reaction temperatures, these substances remain in the ppm range. Long-term studies carried out over a period of 2 654 hours have indicated that catalyst activity and catalyst selectivity have undergone no changes.

Example 6

(Comparative Example)

A pressure tube of stainless steel having a length of about 60 cm and an internal diameter of 1.8 cm was charged with 50 ml of catalyst which had been prepared as described in Example 3, the free volume was filled with wire mesh rings of stainless steel and the catalyst was treated with hydrogen for 24 h at 180° C. under a pressure of 300 bar. By means of a pump, aniline was then metered into the trickle phase in such an amount that the space velocity over the catalyst was 0.5 g of aniline/ml of cat.·h. The hydrogenation was carried out at a pressure of 300 bar using 22 l of H₂/ml of cat.·h. The temperature was varied and kept constant for at least 24 hours at each setting. The reaction mixture was analysed by gas chromatography, as in Example 5:

| Temperature ° C. | ANI % by area | BEN % by area | CYH % by area | CHA % by area | DCHA % by area | R % by area | Loss BEN/CYH/R % |
|---|---|---|---|---|---|---|---|
| 180 | 6.1 | — | 0.10 | 65.88 | 32.89 | 4.77 | 4.87 |
| 220 | — | — | 0.60 | 41.17 | 52.11 | 6.12 | 6.72 |
| 300 | — | 18.20 | 26.50 | 15.40 | 18.84 | 21.06 | 65.76 |

The experimental results show that in the presence of halogen compounds, a hydrogenolysis reaction commences at as low as 180° C. and increases dramatically at a temperature of >220° C. The ratio of hydrocarbons formed is: methane=5.0/ethane=2.4/propane=1.4/butane=1.2/pentane=1.0.

Example 7
(Comparative Example)

A pressure tube of stainless steel having a length of 60 cm and an internal diameter of 1.8 cm was charged with 50 ml of catalyst which had been prepared as described in Example 4, the free volume was filled with wire mesh rings of stainless steel and the catalyst was treated with hydrogen for 24 hours at 180° C. under a pressure of 300 bar. By means of a pump, aniline was then metered into the trickle phase in such an amount that the space velocity over the catalyst was 0.5 g of aniline/ml of cat.·h. The hydrogenation was carried out at a pressure of 300 bar using 22 l of $H_2$/ml of cat.·h. The temperature was varied and kept constant for at least 24 hours at each setting. The reaction mixture was analysed by gas chromatography, as in Example 5:

| Temperature ° C. | ANI % by area | BEN % by area | CYH % by area | CHA % by area | DCHA % by area | R % by area | Loss BEN/CYH/R % |
|---|---|---|---|---|---|---|---|
| 180 | — | — | 0.20 | 55.16 | 43.84 | 0.80 | 1.00 |
| 220 | — | — | 0.80 | 35.18 | 62.12 | 1.90 | 2.70 |
| 300 | — | — | 2.20 | 32.32 | 16.28 | 49.20 | 51.40 |

When the catalyst contains only Ru and no Pd. a drastic hydrogenolysis reaction occurs at reaction temperatures of >220° C. even in the absence of halogen compounds. For this reason, the concomitant use of Pd is absolutely necessary.

What is claimed is:

1. A process for preparing mixtures, in variable ratios, of cyclohexylamines (II) and dicyclohexylamines (III) of the formulas:

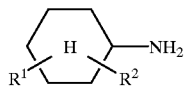
(II)

and

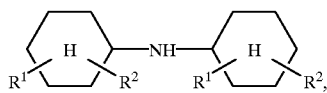
(III)

wherein $R^1$ and $R^2$ are independently hydrogen, $C_1$–$C_4$-alkyl, or $C_1$–$C_4$-alkoxy, comprising catalytically hydrogenating, at a reaction temperature of from 100 to 350° C. and a pressure of from 10 to 400 bar, aromatic amines of the formula (I):

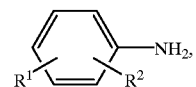
(I)

wherein $R^1$ and $R^2$ are independently hydrogen, $C_1$–$C_4$-alkyl, or $C_1$–$C_4$-alkoxy, in the presence of fixed-bed catalysts that (i) contain as active constituents a total of from 0.05 to 10% by weight of Ru and Pd in a ratio Ru:Pd of 1:30 to 30:1 on supports and (ii) are prepared from starting materials having a total halogen and sulphur content of from 0 to 0.8% by weight.

2. A process according to claim 1 wherein the supports for the catalysts are doped with compounds of the rare earth metals and of manganese, wherein the total amount of rare earth metals and manganese, calculated as metals and based on the total weight of the catalyst, are from 0.05 to 8% by weight and the weight ratio of rare earth metals to manganese are from 5:1 to 1:5.

3. A process according to claim 1 wherein the amount of Ru and Pd is from 0.1 to 5% by weight.

4. A process according to claim 2 wherein the rare earth metal is selected from the group consisting of yttrium, lanthanum, cerium, praseodymium, neodymium, dysprosium, and combinations thereof.

5. A process according to claim 1 wherein the catalytic hydrogenation is carried out at $H_2$ pressures of from 50 to 350 bar and at temperatures of from 150 to 300° C.

6. A process according to claim 1 wherein the catalytic hydrogenation is carried out using an amount of $H_2$ that is from 2 to 100 times the amount necessary for the hydrogenation.

7. A process according to claim 1 carried out continuously in the gas or liquid phase over fixed-bed catalysts at a space velocity over the catalyst of from 0.1 to 3 g of aromatic amine per ml of catalyst per hour.

8. A process according to claim 1 wherein the aromatic amine used is aniline.

* * * * *